United States Patent
Szesni et al.

(10) Patent No.: US 12,269,018 B2
(45) Date of Patent: Apr. 8, 2025

(54) PLATINUM-SULFUR-BASED SHELL CATALYST, PRODUCTION AND USE THEREOF IN THE DEHYDROGENATION OF HYDROCARBONS

(71) Applicant: Clariant International Ltd, Muttenz (CH)

(72) Inventors: Normen Szesni, Rosenheim (DE); Franziska Frankl, Rosenheim (DE); Stefanie Sturm, Bad Aibling (DE); Peter Wasserscheid, Erlangen (DE); Alexander Seidel, Erlangen (DE); Andreas Boesmann, Erlangen (DE)

(73) Assignee: CLARIANT INTERNATIONAL LTD, Muttenz (CH)

( * ) Notice: Subject to any disclaimer, the term of this patent is extended or adjusted under 35 U.S.C. 154(b) by 0 days.

(21) Appl. No.: 17/045,518

(22) PCT Filed: Apr. 10, 2019

(86) PCT No.: PCT/EP2019/059107
§ 371 (c)(1),
(2) Date: Oct. 6, 2020

(87) PCT Pub. No.: WO2019/201706
PCT Pub. Date: Oct. 24, 2019

(65) Prior Publication Data
US 2021/0077984 A1    Mar. 18, 2021

(30) Foreign Application Priority Data
Apr. 18, 2018 (DE) ............... 10 2018 109 254.7

(51) Int. Cl.
*B01J 27/045* (2006.01)
*B01J 6/00* (2006.01)
(Continued)

(52) U.S. Cl.
CPC ............ *B01J 27/045* (2013.01); *B01J 6/001* (2013.01); *B01J 35/397* (2024.01); *B01J 35/51* (2024.01);
(Continued)

(58) Field of Classification Search
CPC .. B01J 27/045; B01J 35/1004; B01J 35/1009; B01J 35/1014; B01J 35/1038; B01J 35/1042; C07C 5/332
See application file for complete search history.

(56) References Cited

U.S. PATENT DOCUMENTS

| 4,082,699 A | 4/1978 | Petrow |
| 4,087,476 A * | 5/1978 | Hayes ................... B01J 23/892 585/444 |

(Continued)

FOREIGN PATENT DOCUMENTS

| CN | 1033949 A * | 7/1989 | ............ B01J 23/622 |
| CN | 101491759 A * | 7/2009 | |

(Continued)

OTHER PUBLICATIONS

Li et al., Machine translation of (CN 101491759), publication date Jul. 29, 2009.*

(Continued)

*Primary Examiner* — Jun Li (57) ABSTRACT

The invention relates to the use of a supported, platinum-containing and sulfur-containing shell catalyst for the partial or complete dehydrogenation of perhydrogenated or partially hydrogenated cyclic hydrocarbons. The present invention also relates to a method for producing a platinum-containing and sulfur-containing shell catalyst and to a platinum-containing and sulfur-containing shell catalyst. The present invention further relates to a method for the (Continued)

partial or complete dehydrogenation of perhydrogenated or partially hydrogenated cyclic hydrocarbons.

21 Claims, 3 Drawing Sheets (51) Int. Cl.
*B01J 35/08* (2006.01)
*B01J 35/30* (2024.01)
*B01J 35/51* (2024.01)
*B01J 35/61* (2024.01)
*B01J 35/63* (2024.01)
*B01J 37/00* (2006.01)
*B01J 37/02* (2006.01)
*B01J 37/18* (2006.01)
*C07C 5/32* (2006.01)
*B01J 21/04* (2006.01)

(52) U.S. Cl.
CPC ........... *B01J 35/612* (2024.01); *B01J 35/613* (2024.01); *B01J 35/633* (2024.01); *B01J 35/635* (2024.01); *B01J 37/0209* (2013.01); *B01J 37/0213* (2013.01); *B01J 37/18* (2013.01); *C07C 5/322* (2013.01); *B01J 21/04* (2013.01)

(56) References Cited

U.S. PATENT DOCUMENTS

| | | |
|---|---|---|
| 4,431,750 A | 2/1984 | McGinnis |
| 4,827,072 A * | 5/1989 | Imai ................ B01J 23/622 585/629 |
| 5,677,260 A * | 10/1997 | Dongara ............... C07C 5/3337 502/328 |
| 5,900,386 A * | 5/1999 | Freund ................. B01J 37/0211 502/340 |
| 7,429,372 B2 | 9/2008 | Pez |
| 7,985,706 B2 | 7/2011 | Okada |
| 10,450,194 B2 | 10/2019 | Boesmann |
| 2010/0190638 A1 | 7/2010 | Hagemeyer |
| 2012/0296111 A1* | 11/2012 | Konigsmann ........ B01J 35/1042 502/262 |
| 2015/0151278 A1* | 6/2015 | Huber .................... C07C 45/29 568/489 |
| 2020/0122125 A1* | 4/2020 | Han ........................ B01J 37/18 |

FOREIGN PATENT DOCUMENTS

| | | | |
|---|---|---|---|
| CN | 105618082 A * | 6/2016 | |
| DE | 19734975 | 3/1999 | |
| DE | 102014223426 | 5/2016 | |
| WO | WO-2008025751 A1 * | 3/2008 | ............ B22F 1/0018 |

OTHER PUBLICATIONS

Van Trimpont, P.A.; et al. Kinetics of Methylcyclohexane Dehydrogenation on Sulfided Commercial Platinum/Alumina and Platinum-Rhenium/Alumina Catalysts, Ind. Eng. Chem. Fundam. 1986. 25. 544-553.

Regalbuto J. R.; et al. "An evaluation of Pt sulfite acid (PSA) as precursor for supported Pt catalysts" Topics in Catalysis 39(3-4), Oct. 2006, 237-243.

Preuster P. K. E.: Dissertation Entwicklung eines Reaktorszur Dehydrierung chemischer Wasserstoffträger als Bestandteil eines dezentralen stationären Energiespeichers, Friedrich-Alexander-Universität Erlangen-Nürnberg, 2017.

* cited by examiner

PLATINUM-SULFUR-BASED SHELL CATALYST, PRODUCTION AND USE THEREOF IN THE DEHYDROGENATION OF HYDROCARBONS

The invention relates to the use of a supported platinum-containing and sulfur-containing shell catalyst for partial or complete dehydrogenation of perhydrogenated or partly hydrogenated cyclic hydrocarbons. The present invention further relates to a process for preparing a platinum-containing and sulfur-containing shell catalyst and to a platinum-containing and sulfur-containing shell catalyst. The present invention also relates to a process for partial or complete dehydrogenation of perhydrogenated or partly hydrogenated cyclic hydrocarbons.

BACKGROUND OF THE INVENTION

Reversible hydrogenation and dehydrogenation of hydrocarbons opens up the possibility in principle of controlled storage and release of hydrogen. Hydrocarbons, for example pi-conjugated systems that enable such reversible storage and release of hydrogen, are frequently referred to as liquid organic hydrogen carriers (LOHCs).

Examples of such LOHCs are disclosed in patent application EP 1 475 349 A2 and include the substance pairs of coronene and (partly) hydrogenated coronene, or the substance pairs of pyrene and (partly) hydrogenated pyrene. Other examples can be found in published specification DE 10 2012 221 809 A1, which suggests the substance pairs of benzyltoluene/(partly) hydrogenated benzyltoluene and dibenzyltoluene/(partly) hydrogenated dibenzyltoluene.

Such systems have the advantage that energy surpluses, for example from renewable production, can be used to generate hydrogen, which is then stored in the form of LOHCs via a hydrogenation reaction. After storage or transport, a dehydrogenation reaction can then be utilized in order to release hydrogen again, which can then be utilized for energy, for example in a fuel cell or in an internal combustion engine.

Catalysts used for the above-described dehydrogenations may be supported precious metal catalysts, especially supported platinum catalysts. DE 10 2012 221 805 A1 describes the use of metal-containing catalysts containing one or more of the metals palladium, nickel, platinum, iridium, ruthenium, cobalt, rhodium, copper, gold, rhenium or iron, in finely divided form on a porous, nonpolar support. EP 1 475 349 A2 proposes, as catalyst, a platinum or rhodium catalyst supported on activated carbon.

In general, supported platinum catalysts are frequently used for dehydrogenation reactions. These may take the form of what are called shell catalysts. Shell catalysts typically have what is called an "eggshell" structure, i.e. the catalytically active substance is present merely in an outer shell of the catalyst support, with the shell extending inward from the outer surface of the support, whereas the inner core of the catalyst support is essentially free of catalytically active substance. Such platinum shell catalysts are typically prepared by applying soluble platinum compounds, for example hexachloroplatinic acid ($H_2PtCl_6 \cdot 6H_2O$), bis(ethylenediamine)platinum chloride [$(NH_2CH_2CH_2NH_2)_2$]$PtCl_2$, tetraammineplatinum chloride $(NH_3)_4PtCl_2$ or diamineplatinum nitrite $(NH_3)_2Pt(NO_2)_2$, to a support. For example, DE 197 34 975 A1 describes inter alia platinum shell catalysts that are prepared by impregnating porous support particles with an aqueous solution of hexachloroplatinum(IV) acid hydrate.

By contrast, EP 1 894 626 A1 describes a supported platinum catalyst in which the platinum is distributed homogeneously over the entire support material. This is achieved in that a sulfur-containing alumina support is first prepared, to which a platinum compound is applied in a second step. EP 1 894 626 A1 also describes the use of the homogeneous catalysts prepared for the dehydrogenation of mono-, bi- and tricyclic hydrogenated aromatics in association with storage of hydrogen.

Owing to the high costs of precious metals, such as platinum, there is a general need to further optimize precious metal efficiency with regard to the abovementioned dehydrogenation applications. This means that there is a need for dehydrogenation methods that enable equal or enhanced conversion rates and high conversions even with a reduced amount of platinum used.

It is an object of the present invention to enable the use of platinum-containing and sulfur-containing shell catalysts for dehydrogenation reactions, wherein the precious metal content of the catalysts can be minimized for the same performance. The term "performance" in the present context is understood to mean mainly the catalytic activity, i.e. firstly the conversion rate based on the amount of the reactant and secondly the selectivity of the catalysts for the desired product.

More particularly, it is an object of the present invention to avoid or to reduce the drastic reduction in reaction rate at high conversions which is typically associated with the dehydrogenation of cyclic hydrocarbons.

It is a further object of the present invention to provide a process for preparing supported platinum shell catalysts, and a supported platinum shell catalyst.

The inventors of the present invention have found that the use of shell catalysts containing not only platinum but also sulfur can distinctly increase dehydrogenation activity, and the activity is maintained even at high conversion rates. This has the advantage that precious metal efficiency can be enhanced, which is associated with more cost-efficient use of the precious metal platinum.

SUMMARY OF THE INVENTION

The invention relates to the use of a shell catalyst for partial or complete dehydrogenation of perhydrogenated or partly hydrogenated cyclic hydrocarbons, wherein the shell catalyst comprises:
  (a) a shaped support body,
  (b) platinum in an amount in the range of 0.01-1% by weight, preferably in the range of 0.1-1.0% by weight, more preferably in the range of 0.2-0.5% by weight, especially in the range of 0.2-0.4% by weight, based on the total weight of the shell catalyst, and
  (c) sulfur,
wherein the atomic ratio of platinum to sulfur is 1:1-1:10, preferably 1:1.5-1:5, more preferably 1:1.5-1:2.5, especially 1:2.

The invention further relates to a process for producing a platinum-containing and sulfur-containing shell catalyst, comprising the following steps:
  (a) applying a solution, preferably an aqueous solution, of platinum sulfite acid ($H_3Pt(SO_3)_2OH$) to a shaped support body to obtain a laden shaped support body,
  (b) optionally washing and/or drying the laden shaped support body, wherein the drying is effected at a temperature in the range from 70° C. to 150° C., especially at about 120° C., over a period of 1 h to 15 h, preferably over a period of 5 h to 10 h, especially over a period of 8 h, (c) calcining the optionally washed and/or dried, laden shaped support body at a temperature in the range from 200° C. to 390° C., preferably in the range from 250° C. to 370° C., especially at about 350° C., over a period of 0.25 h to 5 h, preferably over a period of 0.5 h to 4 h, especially over a period of about 2 h, to obtain a calcined platinum-containing and sulfur-containing shaped shell catalyst body, and (d) reducing the calcined platinum-containing and sulfur-containing shaped shell catalyst body in the presence of hydrogen at a temperature in the range from 200° C. to 500° C., preferably in the range from 300° C. to 450° C., especially at about 400° C., over a period of 0.25 h to 5 h, preferably over a period of 0.5 h to 4 h, especially over a period of about 2 h.

The invention also relates to a shell catalyst comprising (a) a shaped support body, (b) platinum in an amount in the range of 0.01-1% by weight, preferably in the range of 0.1-1.0% by weight, more preferably in the range of 0.2-0.5% by weight, especially in the range of 0.2-0.4% by weight, based on the total weight of the shell catalyst, and (c) sulfur, wherein the atomic ratio of platinum to sulfur is 1:1-1:10, preferably 1:1.5-1:5, more preferably 1:1.5-1:2.5, especially about 1:2.

The invention additionally relates to a process for partial or complete dehydrogenation of perhydrogenated or partly hydrogenated cyclic hydrocarbons with a shell catalyst, wherein the shell catalyst comprises:

(a) a shaped support body, (b) platinum in an amount in the range of 0.01-1% by weight, preferably in the range of 0.1-1.0% by weight, more preferably in the range of 0.2-0.5% by weight, especially in the range of 0.2-0.4% by weight, based on the total weight of the shell catalyst, and (c) sulfur, wherein the atomic ratio of platinum to sulfur is 1:1-1:10, preferably 1:1.5-1:5, more preferably 1:1.5-1:2.5, especially 1:2.

DETAILED DESCRIPTION OF THE INVENTION

In a first embodiment, the invention relates to the use of a shell catalyst for dehydrogenation of cyclic hydrocarbons that can function as organic hydrogen carriers.

The cyclic hydrocarbons are in either perhydrogenated or partly hydrogenated form, meaning that they have only a small number of carbon-carbon multiple bonds, if any.

The perhydrogenated or partly hydrogenated cyclic hydrocarbons may, in addition to carbon and hydrogen, also contain heteroatoms, such as nitrogen. The perhydrogenated or partly hydrogenated cyclic hydrocarbons preferably do not contain any oxygen.

In a preferred embodiment, the perhydrogenated or partly hydrogenated cyclic hydrocarbon is selected from the group consisting of cyclohexane, methylcyclohexane, decalin, perhydrogenated or partly hydrogenated benzyltoluene and perhydrogenated or partly hydrogenated dibenzyltoluene and isomers thereof. In addition, preferred embodiments are perhydrogenated or partly hydrogenated N-alkylated carbazole, preferably perhydrogenated or partly hydrogenated N-ethylcarbazole, N-methylcarbazole and N-propylcarbazole, especially perhydrogenated or partly hydrogenated N-ethylcarbazoles.

The terms benzyltoluene and dibenzyltoluene also include isomers of the compounds mentioned. In addition, the terms benzyltoluene and dibenzyltoluene also include substituted benzyl- or dibenzyltoluenes in which one or both benzyl groups are substituted by one or more groups selected from alkyl groups, such as methyl or ethyl groups, aryl groups, such as phenyl groups, and heteroaryl groups, such as pyridinyl groups.

Partly hydrogenated benzyltoluene includes benzyltoluene compounds in which at least one carbon-carbon double bond of the benzyltoluene has been replaced by a carbon-carbon single bond. Perhydrogenated benzyltoluene includes benzyltoluene compounds in which the carbon-carbon double bonds have been replaced by carbon-carbon single bonds. Examples of partly hydrogenated benzyltoluenes are 1-cyclohexylmethyl-2-methylbenzene, 1-cyclohexylmethyl-3-methylbenzene, 1-cyclohexylmethyl-4-methylbenzene, 1-benzyl-2-methylcyclohexane, 1-benzyl-3-methylcyclohexane, 1-benzyl-4-methylcyclohexane, 1-(1-cyclohexenylmethyl)-2-methylbenzene, 1-(1-cyclohexenylmethyl)-3-methylbenzene, 1-(1-cyclohexenylmethyl)-4-methylbenzene, 1-(1,3-cyclohexadienylmethyl)-2-methylbenzene, 1-(1,3-cyclohexadienylmethyl)-3-methylbenzene and 1-(1,3-cyclohexadienylmethyl)-4-methylbenzene.

Examples of perhydrogenated benzyltoluenes are 1-cyclohexylmethyl-2-methylcyclohexane, 1-cyclohexylmethyl-3-methylcyclohexane and 1-cyclohexylmethyl-4-methylcyclohexane.

A partly hydrogenated dibenzyltoluene includes any dibenzyltoluene compound in which at least one carbon-carbon double bond of the dibenzyltoluene has been replaced by a carbon-carbon single bond. A perhydrogenated dibenzyltoluene includes any dibenzyltoluene compound in which all carbon-carbon double bonds have been replaced by carbon-carbon single bonds. Examples of partly hydrogenated dibenzyltoluene are 1-benzyl-3-(cyclohexylmethyl)-5-methylbenzene, (5-methyl-1,3-phenylene)bis(methylene)dicyclohexane, 1-benzyl-4-(cyclohexylmethyl)-2-methylbenzene, (2-methyl-1,4-phenylene)bis(methylene)dicyclohexane, 2-benzyl-4-(cyclohexylmethyl)-1-methylbenzene, (4-methyl-1,3-phenylene)bis(methylene)dicyclohexane, 1-benzyl-3-(cyclohexylmethyl)-2-methylbenzene, (2-methyl-1,3-phenylene)bis(methylene)dicyclohexane, 1-benzyl-2-(cyclohexylmethyl)-4-methylbenzene, (4-methyl-1,2-phenylene)bis(methylene)dicyclohexane, 1-benzyl-3-(1-cyclohexenylmethyl)-5-methylbenzene and 1-benzyl-3-(1,3-cyclohexadienylmethyl)-5-methylbenzene. Examples of perhydrogenated dibenzyltoluene are (5-methylcyclohexane-1,3-diyl)bis(methylene)dicyclohexane, (2-methylcyclohexane-1,4-diyl)bis(methylene)dicyclohexane, (4-methylcyclohexane-1,3-diyl)bis(methylene)dicyclohexane, (2-methylcyclohexane-1,3-diyl)bis(methylene)dicyclohexane and (4-methylcyclohexane-1,2-diyl)bis(methylene)dicyclohexane.

A partly hydrogenated N-alkylcarbazole, such as N-ethylcarbazole, includes any N-alkylcarbazole in which at least one carbon-carbon double bond present therein has been replaced by a carbon-carbon single bond. A perhydrogenated N-alkylcarbazole, such as N-ethylcarbazole, includes any N-alkylcarbazole in which all carbon-carbon double bond present therein have been replaced by carbon-carbon single bonds. Examples of partly hydrogenated N-ethylcarbazole are 9-ethyl-2,3,4,9-tetrahydro-1H-carbazole, 9-ethyl-2,3,4,5,6,9-hexahydro-1H-carbazole, 9-ethyl-2,3,4,5,6,7,8,9-octahydro-1H-carbazole and 9-ethyl-2,3,4,4a,5,6,7,8,9,9a-decahydro-1H-carbazole. Perhydrogenated N-ethylcarbazole is, for example, 9-ethyldodecahydro-1H-carbazole.

The dehydrogenation may be partial or complete. The dehydrogenation is preferably complete. Dehydrogenation is complete when fully saturated carbocyclyl or heterocyclyl radicals (for example cyclohexyl or piperidinyl radicals) or partly saturated carbocyclyl or heterocyclyl radicals (for example cyclohexenyl or dihydropyridyl radicals) are converted to the corresponding aromatic form (for example phenyl or pyridyl radicals).

In a preferred embodiment, the dehydrogenation is performed continuously in a reactor selected from a fixed bed reactor, a flow bed reactor or a fluidized bed reactor, preferably a fixed bed reactor.

The dehydrogenation is preferably effected at a temperature in the range from 200° C. to 400° C., more preferably at a temperature in the range from 230° C. to 330° C., especially at a temperature in the range from 260° C. to 310° C. The dehydrogenation is preferably performed at a pressure in the range from 1 to 5 bar, more preferably in the range from 2 to 4 bar, especially at a pressure of about 3 bar.

The liquid hourly space velocity (LHSV) is preferably in the range between 0.5 and 3/h, more preferably in the range between 1 and 2/h. For better removal of the $H_2$ in the reaction, the reactor may be operated horizontally and may be open at the top; in this case, the catalyst is fixed by a mesh. The $H_2$ can also be driven out by gases such as $N_2$, Ar, but also $H_2$.

The shell catalyst used in accordance with the invention comprises
 (a) a shaped support body,
 (b) platinum in an amount in the range of 0.01-1% by weight, preferably in the range of 0.1-1.0% by weight, more preferably in the range of 0.2-0.5% by weight, especially in the range of 0.2-0.4% by weight, based on the total weight of the shell catalyst, and
 (c) sulfur,
wherein the atomic ratio of platinum to sulfur is 1:1-1:10, preferably 1:1.5-1:5, especially about 1:2.

The shaped support body of the shell catalyst may take the form of extrudates, such as strands or ribbed strands, tablets, rings, ring tablets, spheres, pellets, honeycombs, or granules. The shaped support body of the shell catalyst preferably takes the form of a tablet, sphere, ring, pellet or granule, especially of a sphere. The shaped bodies may have diameters in the range from 0.05 mm to 50 mm. Shaped bodies in sphere form typically have a diameter in the range from 0.1 mm to 20 mm, preferably in the range from 0.5 mm to 10 mm, especially in the range from 1 mm to 6 mm. Shaped bodies in extruded form may have a length, for example, in the range from 2 mm to 12 mm, preferably in the range from 3 mm to 10 mm, especially in the range from 4 mm to 7 mm. Shaped bodies in the form of tablets typically have a diameter in the range from 1 mm to 10 mm, preferably in the range from 1.5 mm to 8 mm and more preferably in the range from 4 mm to 6 mm, and a height h in the range from 1 mm to 10 mm, preferably in the range from 1.5 mm to 8 mm and more preferably in the range from 3 mm to 4 mm.

The shell catalyst has an "eggshell" structure, i.e. the platinum and the sulfur are present essentially in an outer shell of the shaped support body, with the shell extending inward from the outer surface of the shaped support body, whereas the inner core of the shaped support body is essentially free of platinum and sulfur. What is meant by "outer surface" is the macroscopic interface between the solid material of the shaped support body and the gaseous or liquid environment.

The thickness of the (outer) shell of the shell catalyst is in the range from 20 µm to 500 µm, preferably in the range from 40 µm to 250 µm, especially in the range from 60 µm to 120 µm.

The thickness of the outer shell can be ascertained by examining the spatial distribution of platinum and sulfur in the shell catalyst. For this purpose, for example, a section through the shaped support body is performed, for example with a knife. In the case of spherical shaped bodies, the section is ideally made in such a way as to result, as far as possible, in two hemispheres of equal size with circular section faces. The resulting section faces may subsequently be examined in a scanning electron microscope. With the aid of the method of energy-dispersive x-ray spectroscopy (EDX spectroscopy), it is possible to ascertain the local distribution of platinum and sulfur, for example, along a line across the section face that can be chosen freely. In the case of circular section faces, the line is then chosen, as far as possible, such that it lies at right angles to the circle tangent and leads through the center of the circle. The element-specific intensities along the line (EDX linescan) reflect the relative amount of the elements platinum and sulfur as a function of the location, and can be used for a determination of the shell thickness. The spatial resolution of the EDX method is typically within the range from about 2 to 10 µm.

Figure 2A:
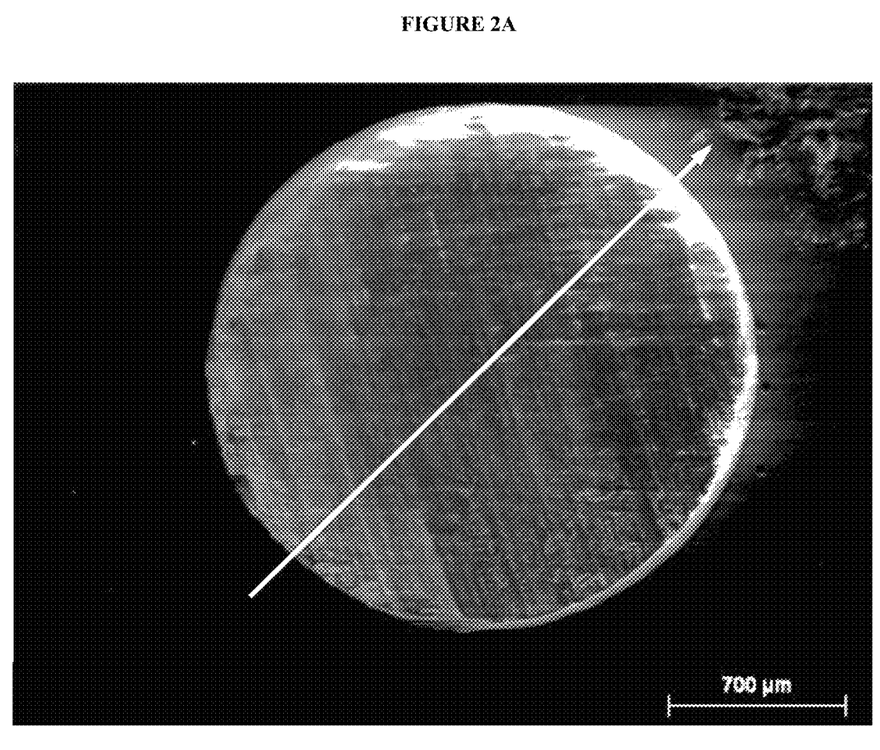
FIG. 2 shows a scanning electron micrograph of a section through the catalyst of the invention from example 1 (FIG. 2a) and the intensity curve for the elements platinum and sulfur, determined by EDX linescan for this catalyst (FIG. 2b).
Figure 2B:
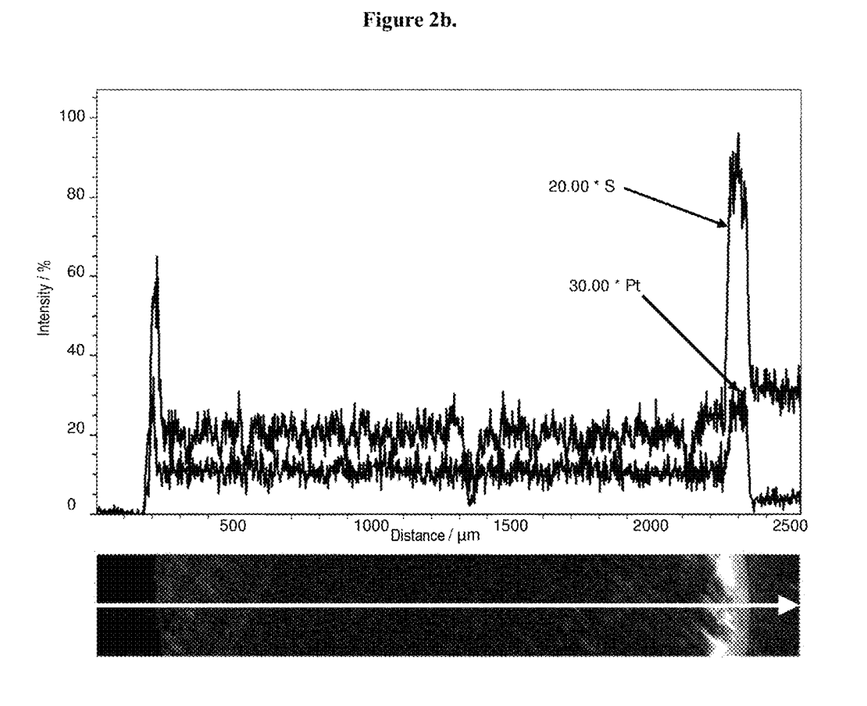

An EDX linescan along a line across a section face through a spherical shaped body is shown by way of example in FIG. 2b. From left to right, the intensity curve shows firstly a significant relative increase in the intensity of platinum and sulfur, followed by a significant relative decrease in the intensity of platinum and sulfur. In order to be able to better show the effect, the intensity curve for platinum is shown in 30-fold magnification, and that for sulfur in 20-fold magnification. Preferably, the EDX intensity of platinum and sulfur decreases completely to 0, i.e. taking account of the detection limit of the EDX method. This means that it is preferably no longer possible to detect any platinum or sulfur by the EDX method in the region that follows the significant relative decrease. It is possible to use the location of the two changes in intensity or their local differential to determine a first value for the shell thickness. In the middle part of the intensity curve, the intensity of platinum and sulfur is virtually constant. In the right-hand part of the intensity curve, there is again firstly a significant relative increase in the intensity of platinum and sulfur, followed by a significant relative decrease in the intensity of platinum and sulfur. It is possible to use the location of these two changes in intensity or their local differential to determine a second value for the shell thickness. Therefore, two measured values for shell thickness are obtained per line. Typically, the shell thickness is determined for a multitude, typically for 2 to 20, for example for four, section faces of shaped catalyst bodies. The values obtained for shell thickness (in µm) are used to form the arithmetic average.

The outer shell of the shell catalyst preferably comprises 85% by weight or more, preferably 90% by weight or more, especially 95% by weight or more, of the total amount of platinum present in the shell catalyst, and 85% by weight or more, preferably 90% by weight or more, especially 95% by weight or more, of the total amount of sulfur present in the shell catalyst. More preferably, essentially no platinum or sulfur can be detected in the inner core by the EDX method.

The shaped support body preferably comprises alumina, for example $Al_2O_3$, silicon dioxide ($SiO_2$), titanium dioxide ($TiO_2$), zirconium dioxide ($ZrO_2$), silicon carbide (SiC) or mixtures thereof. More preferably, the shaped support body comprises alumina. More preferably, the alumina is selected from gamma-alumina, theta-alumina, delta-alumina, alpha-alumina or mixtures thereof, and is especially gamma-alumina.

The shell catalyst preferably has a BET surface area in the range from 1 $m^2$/g to 300 $m^2$/g, more preferably 1 $m^2$/g to 250 $m^2$/g, even more preferably in the range from 2 $m^2$/g to 150 $m^2$/g, especially in the range from 3 $m^2$/g to 100 $m^2$/g. BET surface area is determined by the single-point nitrogen method in accordance with DIN 66132.

The pore volume of the shell catalyst, determined by Hg intrusion methods to DIN 66133, is preferably 0.1 to 1.0 $cm^3$/g, especially 0.3 to 0.6 $cm^3$/g.

The invention also provides a process for preparing a platinum-containing and sulfur-containing shell catalyst.

In a step (a), a solution of platinum sulfite acid is applied to a shaped support body. Platinum sulfite acid is frequently also referred to as platinum-sulfurous acid and is usually specified by the empirical formula $H_3Pt(SO_3)_2OH$.

Aqueous solutions of platinum sulfite acid ($H_3Pt(SO_3)_2OH$) are commercially available and frequently have a concentration of 5 to 20 percent by weight. The solutions may additionally contain sulfurous acid. The solution of platinum sulfite acid used in step (a) may have a concentration in the range from 0.5 to 5 percent by weight and is typically prepared by diluting a commercially available concentrated solution to the desired concentration with the aid of water.

The shaped support body preferably comprises alumina ($Al_2O_3$), silicon dioxide ($SiO_2$), titanium dioxide ($TiO_2$), zirconium dioxide ($ZrO_2$), silicon carbide (SiC) or mixtures thereof. Even more preferably, the shaped support body comprises alumina ($Al_2O_3$). The alumina is preferably selected from gamma-alumina, theta-alumina, delta-alumina, alpha-alumina or mixtures thereof, and is especially gamma-alumina.

The shaped support body of the shell catalyst may take the form of extrudates, such as strands or ribbed strands, tablets, rings, ring tablets, spheres, pellets, honeycombs, or granules. The shaped support body of the shell catalyst preferably takes the form of a tablet, sphere, pellet or granule, especially of a sphere.

In one embodiment, the solution of platinum sulfite acid is applied to the shaped support body by impregnation. For the impregnation of the shaped support bodies, these are generally mixed with a platinum sulfite acid-containing solution. Preference is given here to employing what is called the incipient wetness method. In this method, also referred to as pore filling method, the shaped support body is contacted with a solution volume corresponding to its pore volume. This means that the amount of the platinum sulfite acid-containing solution used for impregnation (i.e. of the impregnation solution) is matched to the adsorption volume of the support such that the entire amount of the impregnation solution is absorbed by the shaped support body and there is no longer any excess solution present after the impregnation. In order to ascertain the amount of solution needed for the incipient wetness impregnation, preliminary tests are conducted with water. The water absorption of the shaped support bodies is determined here until the pores are filled but the shaped support bodies are just wet on the surface, i.e. until the shaped support bodies have a moist shine. The absorption volume determined by this method is applied to the amount of impregnation solution.

As an alternative to the incipient wetness method, it is also possible to apply the platinum sulfite acid-containing solution to the shaped support body by using other methods known to the person skilled in the art (for example spray application, diffusion impregnation, chemical vapor deposition (CVD)).

The spray application can be effected, for example, by the method described in published specification DE 10 2007 025 356 A1. For this purpose, shaped support bodies are sprayed with a platinum sulfite acid-containing solution in a spray chamber. The spray application can be performed, for example, with Innojet equipment such as the "Innojet Aircoater". This involves circulating the shaped catalyst body in the spray chamber in the form of two opposing spiral movements in a circular arrangement by means of a suitable booster (e.g. Innojet Vulcano). The method is described in "Easy Coating: Grundlagen and Trends beim Coating pharmazeutischer Produkte" [Easy Coating: Basics and Trends in the Coating of Pharmaceutical Products] editors: Mont Kumpugdee-Vollrath, Jens-Peter Krause; Vieweg+Teubner Verlag; 1st edition 2011, pages 120-132. The platinum-containing solution can be introduced into the spray chamber, for example, via spray nozzles in a vertical arrangement.

After the platinum sulfite acid-containing solution has been applied to the shaped support bodies, the laden shaped support bodies can be washed in an optional step (b) and then dried. It is also possible to dispense with washing of the laden shaped support bodies.

The optional drying of the optionally washed shaped support bodies can be effected, for example, at a temperature in the range from 70° C. to 150° C., especially at about 120° C., over a period of 1 h to 15 h, preferably over a period of 5 h to 10 h, especially over a period of 8 h.

In a particularly preferred embodiment, drying is effected over a period of 5 h to 10 h at a temperature in the range from 70° C. to 150° C.

The steps of applying the platinum sulfite acid-containing solution to the shaped support body and the optional washing and drying may be performed repeatedly in succession until a desired target loading with platinum is attained. "Target loading" is understood to mean the platinum content in the calcined and reduced shell catalyst in % by weight, based on the total weight of the calcined and reduced shell catalyst.

The target loading with platinum is in the range from 0.01% to 1% by weight, preferably in the range from 0.1% to 1.0% by weight, more preferably in the range from 0.2% to 0.5% by weight, especially in the range from 0.2% to 0.4% by weight, based on the total weight of the shell catalyst.

The number of impregnations depends on factors including the absorption capacity of the shaped support body (i.e. its pore volume) and the desired target loading. There is generally only one impregnation.

The laden and optionally washed and dried shaped support bodies are subjected to a calcination in a step (c). The calcination is preferably effected at a temperature in the range from 200° C. to 390° C., preferably in the range from 250° C. to 370° C., especially at about 350° C., over a period of 0.25 h to 5 h, preferably over a period of 0.5 h to 4 h, especially over a period of about 2 h.

In a preferred embodiment, the calcination is effected at a temperature in the range from 250° C. to 370° C. over a period of 0.5 h to 4 h, especially at about 350° C. over a period of about 2 h.

The calcined platinum-containing and sulfur-containing shaped shell catalyst bodies obtained in step (c) are then reduced in a step (d).

The reduction is preferably effected at a temperature in the range from 200° C. to 500° C., more preferably in the range from 300° C. to 450° C., especially preferably at about 400° C., over a period of 0.25 h to 5 h, preferably over a period of 0.5 h to 4 h, especially over a period of about 2 h.

In a preferred embodiment, the reduction is effected at a temperature in the range from 300° C. to 450° C. over a period of 0.5 h to 4 h, especially at about 400° C. over a period of about 2 h.

The invention also provides a shell catalyst comprising
(a) a shaped support body,
(b) platinum in an amount in the range of 0.01-1% by weight, preferably in the range of 0.1-1.0% by weight, more preferably in the range of 0.2-0.5% by weight, especially in the range of 0.2-0.4% by weight, based on the total weight of the shell catalyst, and
(c) sulfur,
wherein the atomic ratio of platinum to sulfur is 1:1-1:10, preferably 1:1.5-1:5, more preferably 1:1.5-1:2.5, especially 1:2.

The shaped support body of the shell catalyst may take the form of extrudates, such as strands or ribbed strands, tablets, rings, ring tablets, spheres, pellets, honeycombs, or granules. The shaped support body of the shell catalyst may take the form of a tablet, sphere, pellet or granule, especially of a sphere.

The shell catalyst preferably has an outer shell comprising the platinum and the sulfur. The thickness of the outer shell is in the range from 20 µm to 500 µm, preferably in the range from 40 µm to 250 µm, especially in the range from 60 µm to 120 µm.

The outer shell of the shell catalyst preferably comprises 85% by weight or more, preferably 90% by weight or more, especially 95% by weight or more, of the total amount of platinum and sulfur present in the shell catalyst.

The shaped support body preferably comprises alumina, for example $Al_2O_3$, silicon dioxide ($SiO_2$), titanium dioxide ($TiO_2$), zirconium dioxide ($ZrO_2$), silicon carbide (SiC) or mixtures thereof. Even more preferably, the shaped support body comprises alumina ($Al_2O_3$). The alumina is preferably selected from gamma-alumina, theta-alumina, delta-alumina, alpha-alumina or mixtures thereof, and is especially gamma-alumina.

The shell catalyst preferably has a BET surface area in the range from 1 $m^2/g$ to 300 $m^2/g$, more preferably 1 $m^2/g$ to 250 $m^2/g$, even more preferably in the range from 2 $m^2/g$ to 150 $m^2/g$, especially in the range from 3 $m^2/g$ to 100 $m^2/g$.

The pore volume of the shell catalyst, determined by Hg intrusion methods to DIN 66133, is preferably 0.1 to 1.0 $cm^3/g$, especially 0.3 to 0.6 $cm^3/g$.

The invention also provides a process for dehydrogenating cyclic hydrocarbons that can function as organic hydrogen carriers with the shell catalyst of the invention.

The cyclic hydrocarbons are in either perhydrogenated or partly hydrogenated form, meaning that they have only a small number of carbon-carbon multiple bonds, if any.

The perhydrogenated or partly hydrogenated cyclic hydrocarbons may, in addition to carbon and hydrogen, also contain heteroatoms, such as nitrogen. The perhydrogenated or partly hydrogenated cyclic hydrocarbons preferably do not contain any oxygen.

In a preferred embodiment, the perhydrogenated or partly hydrogenated cyclic hydrocarbon is selected from the group consisting of cyclohexane, methylcyclohexane, decalin, perhydrogenated or partly hydrogenated benzyltoluene and perhydrogenated or partly hydrogenated dibenzyltoluene and isomers thereof. In addition, preferred embodiments are perhydrogenated or partly hydrogenated N-alkylated carbazole, preferably perhydrogenated or partly hydrogenated N-ethylcarbazole, N-methylcarbazole and N-propylcarbazole, especially perhydrogenated or partly hydrogenated N-ethylcarbazoles.

The terms benzyltoluene and dibenzyltoluene also include isomers of the compounds mentioned. In addition, the terms benzyltoluene and dibenzyltoluene also include substituted benzyl- or dibenzyltoluenes in which one or both benzyl groups are substituted by one or more groups selected from alkyl groups, such as methyl or ethyl groups, aryl groups, such as phenyl groups, and heteroaryl groups, such as pyridinyl groups.

Partly hydrogenated benzyltoluene includes benzyltoluene compounds in which at least one carbon-carbon double bond of the benzyltoluene has been replaced by a carbon-carbon single bond. Perhydrogenated benzyltoluene includes benzyltoluene compounds in which the carbon-carbon double bonds have been replaced by carbon-carbon single bonds. Examples of partly hydrogenated benzyltoluenes are 1-cyclohexylmethyl-2-methylbenzene, 1-cyclohexylmethyl-3-methylbenzene, 1-cyclohexylmethyl-4-methylbenzene, 1-benzyl-2-methylcyclohexane, 1-benzyl-3-methylcyclohexane, 1-benzyl-4-methylcyclohexane, 1-(1-cyclohexenylmethyl)-2-methylbenzene, 1-(1-cyclohexenylmethyl)-3-methylbenzene, 1-(1-cyclohexenylmethyl)-4-methylbenzene, 1-(1,3-cyclohexadienylmethyl)-2-methylbenzene, 1-(1,3-cyclohexadienylmethyl)-3-methylbenzene and 1-(1,3-cyclohexadienylmethyl)-4-methylbenzene.

Examples of perhydrogenated benzyltoluenes are 1-cyclohexylmethyl-2-methylcyclohexane, 1-cyclohexylmethyl-3-methylcyclohexane and 1-cyclohexylmethyl-4-methylcyclohexane.

A partly hydrogenated dibenzyltoluene includes any dibenzyltoluene compound in which at least one carbon-carbon double bond of the dibenzyltoluene has been replaced by a carbon-carbon single bond. A perhydrogenated dibenzyltoluene includes any dibenzyltoluene compound in which all carbon-carbon double bonds have been replaced by carbon-carbon single bonds. Examples of partly hydrogenated dibenzyltoluene are 1-benzyl-3-(cyclohexylmethyl)-5-methylbenzene, (5-methyl-1,3-phenylene)bis(methylene)dicyclohexane, 1-benzyl-4-(cyclohexylmethyl)-2-methylbenzene, (2-methyl-1,4-phenylene)bis(methylene)dicyclohexane, 2-benzyl-4-(cyclohexylmethyl)-1-methylbenzene, (4-methyl-1,3-phenylene)bis(methylene)dicyclohexane, 1-benzyl-3-(cyclohexylmethyl)-2-methylbenzene, (2-methyl-1,3-phenylene)bis(methylene)dicyclohexane, 1-benzyl-2-(cyclohexylmethyl)-4-methylbenzene, (4-methyl-1,2-phenylene)bis(methylene)dicyclohexane, 1-benzyl-3-(1-cyclohexenylmethyl)-5-methylbenzene and 1-benzyl-3-(1,3-cyclohexadienylmethyl)-5-methylbenzene. Examples of perhydrogenated dibenzyltoluene are (5-methylcyclohexane-1,3-diyl)bis(methylene)dicyclohexane, (2-methylcyclohexane-1,4-diyl)bis(methylene)dicyclohexane, (4-methylcyclohexane-1,3-diyl)bis(methylene)dicyclohexane, (2-methylcyclohexane-1,3-diyl)bis(methylene)dicyclohexane and (4-methylcyclohexane-1,2-diyl)bis(methylene)dicyclohexane.

A partly hydrogenated N-alkylcarbazole, such as N-ethylcarbazole, includes any N-alkylcarbazole in which at least one carbon-carbon double bond present therein has been replaced by a carbon-carbon single bond. A perhydrogenated N-alkylcarbazole, such as N-ethylcarbazole, includes any N-alkylcarbazole in which all carbon-carbon double bond present therein have been replaced by carbon-carbon single bonds. Examples of partly hydrogenated N-ethylcarbazole are 9-ethyl-2,3,4,9-tetrahydro-1H-carbazole, 9-ethyl-2,3,4,5,6,9-hexahydro-1H-carbazole, 9-ethyl-2,3,4,5,6,7,8,9-octahydro-1H-carbazole and 9-ethyl-2,3,4,4a,5,6,7,8,9,9a-decahydro-1H-carbazole. Perhydrogenated N-ethylcarbazole is, for example, 9-ethyldodecahydro-1H-carbazole.

The dehydrogenation may be partial or complete. The dehydrogenation is preferably complete. Dehydrogenation is complete when fully saturated carbocyclyl or heterocyclyl radicals (for example cyclohexyl or piperidinyl radicals) or partly saturated carbocyclyl or heterocyclyl radicals (for example cyclohexenyl or dihydropyridyl radicals) are converted to the corresponding aromatic form (for example phenyl or pyridyl radicals).

In a preferred embodiment, the dehydrogenation is performed continuously in a reactor selected from a fixed bed reactor, a flow bed reactor or a fluidized bed reactor, preferably a fixed bed reactor.

The dehydrogenation is preferably effected at a temperature in the range from 200° C. to 400° C., more preferably at a temperature in the range from 230° C. to 330° C., especially at a temperature in the range from 260° C. to 310° C. The dehydrogenation is preferably performed at a pressure in the range from 1 to 5 bar, more preferably in the range from 2 to 4 bar, especially at a pressure of about 3 bar.

The liquid hourly space velocity (LHSV) is preferably in the range between 0.5 and 3/h, more preferably in the range between 1 and 2/h. For better removal of the $H_2$ in the reaction, the reactor may be operated horizontally and may be open at the top; in this case, the catalyst is fixed by a mesh. The $H_2$ can also be driven out by gases such as $N_2$, Ar, but also $H_2$.

DESCRIPTION OF THE FIGURES

FIG. 1 shows the catalytic activity of various catalysts. What is shown is the degree of dehydrogenation of perhydrogenated dibenzyltoluene over a period of 2 hours under the following conditions: temperature 310° C., pressure: ambient pressure, ratio of platinum content to perhydrogenated dibenzyltoluene: 0.1 mol %.

DETERMINATION OF PHYSICAL PARAMETERS

The physical parameters cited in the present invention, unless stated otherwise, are determined as described below:

Determination of BET surface area: BET surface area is determined by the single-point nitrogen method in accordance with DIN 66132.

Pore volume: Pore volume is determined by mercury intrusion to DIN 66133.

Shell thickness: Shell thickness is determined by EDX linescan.

For this purpose, the sample is cut down the middle into two halves with a sharp knife and then ground flat with a rotating abrasive paper. The adhering dust is removed with oil-free compressed air. After this sample preparation, the sample is fixed on the sample holder with the ground surface upward. Subsequently, the sample is transferred into a scanning electron microscope. The following parameters are used for the EDX linescan:

Scanning electron microscope: LEO 1530 from LEO Zeiss
Detector: Quantax with XFlash 4010 from Bruker
Voltage:
Aperture:
Working distance: about 16 mm
Magnification: about 55-fold
Measurement duration: about 10-30 min
Distance from measurement point to measurement point: 2-5 μm Ignition loss: The determinations of ignition loss are effected by determining the weight of about 1-2 g of a sample of the material to be analyzed and then heating it to 900° C. under ambient atmosphere and storing it at this temperature for 3 h. Subsequently, the sample is cooled down under protective atmosphere and the remaining weight is measured. The difference in weight before and after thermal treatment corresponds to the ignition loss.

Platinum Content/Sulfur Content:

Determination of platinum: A suitable starting weight of the sample is digested in concentrated hydrochloric acid and concentrated nitric acid in a ratio of 3:1 in a microwave oven at 180° C. for 15 minutes and then cooled back down to about 20° C. A suitable amount of water is added to prepare a standard solution and centrifuged to obtain clear solutions that are analyzed using the ICP instrument ("SPECTRO ARCOS" type from Spectro Analytical Instruments GmbH). In the context of the present invention, platinum contents are based on the catalysts after ignition loss.

Determination of Sulfur:

A homogenized pulverulent sample (weight: 100 to 200 mg) is analyzed in the CS-200 instrument from Leco. The determination is effected via combustion of the bound sulfur in an oxygen stream and quantitative analysis of the product gases by means of an infrared measurement cell. In the context of the present invention, sulfur contents are based on the catalysts after ignition loss.

Platinum Dispersion:

Platinum dispersion is determined by carbon monoxide (CO) chemisorption and subsequent methanation of the metal-bound CO. For this purpose, the platinum catalyst is first oxidized with synthetic air, reduced with an excess of hydrogen and saturated with carbon monoxide at room temperature. Excess carbon monoxide is removed in a hydrogen stream. The carbon monoxide chemisorbed on the precious metal is quantitatively methanated in the hydrogen atmosphere. The methane is determined quantitatively in a flame ionization detector (Trace 1300 GC, Thermo Scientific).

EXAMPLES

The invention is elucidated in detail by the nonlimiting examples that follow. Even though these examples describe specific embodiments of the invention, they serve merely to illustrate the invention and should not be regarded as limiting the invention in any way. As the person skilled in the art is aware, numerous changes can be made thereto without departing from the scope of protection of the invention as defined by the appended patent claims.

Comparative Example 1 (Pt Eggshell Catalyst Prepared Via Spray Application)

By the method described in DE 102007025356 A1, an aqueous solution of $K_2[Pt(OH)_6]$ is applied to an alumina support (delta/theta-$Al_2O_3$; spheres with a diameter of 2 to 4 mm, BET 115 $m^2$/g; pore volume 0.8 ml/g; bulk density 560 g/l). For this purpose, 0.62 gram of $K_2[Pt(OH)_6]$ is dissolved in 150 ml of water, and the solution obtained is then applied to 100 g of the support by spray application. The support is continually agitated in the fluidized bed during the application. Subsequently, the solids obtained are calcined at 400° C. The Pt content of the catalyst is 0.3% by weight. The Pt dispersion is 32%, the BET surface area 115 $m^2$/g.

Comparative Example 2 (Pt Eggshell Catalyst Prepared Via Spray Application) in Reduced Form The catalyst from comparative example 1 is reduced in a hydrogen stream at about 450° C. for a period of 15 hours. The platinum content is 0.3% by weight. The Pt dispersion is 30%, the BET surface area 115 $m^2$/g.

Comparative Example 3 (Pt Eggshell Catalyst Prepared Via Spray Application)

By the method described in DE102007025356 A1, an aqueous solution of $K_2[Pt(OH)_6]$ is applied to an alumina support (gamma-$Al_2O_3$; spheres with a diameter of 1 to 2 mm; BET 290 $m^2$/g; pore volume 0.45 ml/g; bulk density 800 g/l). For this purpose, 0.62 gram of $K_2[Pt(OH)_6]$ is dissolved in 150 ml of water, and the solution obtained is then applied to 100 g of the support by spray application. The support is continually agitated in the fluidized bed during the application. Subsequently, the solids obtained are calcined at 400° C. The Pt content of the catalyst is 0.3% by weight. The Pt dispersion is 29%, the BET surface area 290 $m^2$/g.

Comparative Example 4 (Pt Eggshell Catalyst Prepared Via Impregnation)

120 ml of an aqueous solution of $H_2PtCl_6$ (0.0025 g/ml, based on Pt) is contacted at room temperature under continual agitation with 100 g of an alumina support (delta/theta-$Al_2O_3$; spheres with a diameter of 2 to 4 mm, BET 115 $m^2$/g; pore volume 0.8 ml/g; bulk density 560 g/l). The volume of the aqueous solution corresponds at least to the water absorption capacity of the support. After 15 min, the supernatant solution is removed and the support is washed with water to remove the chloride released. This is followed by drying at 150° C. to a relative drying loss of 8% by weight, followed by calcining at 500° C. The Pt content of the catalyst is 0.3%. The Pt dispersion is 52%, the BET surface area 115 $m^2$/g.

Comparative Example 5 (Through-Impregnated Catalyst Produced Via Incipient Wetness Method)

Step 1: Application of Sulfur to the Support
100 g of an alumina support (delta/theta-$Al_2O_3$; spheres with a diameter of 2 to 4 mm, BET 115 $m^2$/g; pore volume 0.8 ml/g; bulk density 560 g/l) are impregnated at room temperature with an aqueous ammonium sulfate solution (concentration 0.38 mol/l). The volume of the aqueous solution corresponds at least to the water absorption capacity of the support. The impregnated supports are then dried at 120° C. over a period of 3 hours and then calcined at 350° C. over a period of 3 hours. The sulfur content is 0.5% by weight.

Step 2: Application of Platinum to the Support
The sulfur-containing supports are then contacted at room temperature under continual agitation with 70 ml of an aqueous solution of $H_2PtCl_6$, pH 2.0 (0.0085 g/ml, based on Pt). The impregnated supports are then dried at 120° C. over a period of 3 hours and then calcined at 400° C. over a period of 3 hours. Then the calcined supports were reduced in a hydrogen stream in a flow apparatus at about 450° C. for a period of 15 hours. The platinum content is 0.6% by weight. The Pt dispersion is 49%, the BET surface area 115 $m^2$/g.

Comparative Example 6 (Through-Impregnated Catalyst Produced Via Incipient Wetness Method)

Step 1: Application of Sulfur to the Support
100 g of an alumina support (gamma-$Al_2O_3$; spheres with a diameter of 1 to 2 mm; BET 290 $m^2$/g; pore volume 0.45 ml/g; bulk density 800 g/l) are impregnated at room temperature with an aqueous ammonium sulfate solution (concentration 0.38 mol/l). The volume of the aqueous solution corresponds at least to the water absorption capacity of the support. The impregnated supports are then dried at 120° C. over a period of 3 hours and then calcined at 350° C. over a period of 3 hours. The sulfur content is 0.5% by weight.

Step 2: Application of Platinum to the Support
The sulfur-containing supports are then contacted at room temperature under continual agitation with 50 ml of an aqueous solution of $H_2PtCl_6$, pH 2.0 (0.012 g/ml, based on Pt). Subsequently, excess liquid is removed with the aid of an evaporator. The impregnated supports are then dried at 120° C. over a period of 3 hours and then calcined at 400° C. over a period of 3 hours. Then the calcined supports were reduced in a hydrogen stream in a flow apparatus at about 450° C. for a period of 15 hours. The platinum content is 0.6% by weight. The Pt dispersion is 47%, the BET surface area 290 $m^2$/g.

Comparative Example 7 (Through-Impregnated Catalyst)

Step 1: Application of Sulfur to the Support
100 g of an alumina support (delta/theta-$Al_2O_3$; spheres with a diameter of 2 to 4 mm, BET 115 $m^2$/g; pore volume 0.8 ml/g; bulk density 560 g/l) are impregnated at room temperature with an aqueous ammonium sulfate solution (concentration 0.38 mol/l). The volume of the aqueous solution corresponds at least to the water absorption capacity of the support. Subsequently, excess liquid is removed with the aid of an evaporator. The impregnated supports are then dried at 120° C. over a period of 3 hours and then calcined at 350° C. over a period of 3 hours. The sulfur content is 0.25% by weight.

Step 2: Application of Platinum to the Support
The sulfur-containing supports are then contacted at room temperature under continual agitation with 70 ml of an aqueous solution of $H_2PtCl_6$, pH 2.0 (0.043 g/ml, based on Pt). Subsequently, excess liquid is removed with the aid of an evaporator. The impregnated supports are then dried at 120° C. over a period of 3 hours and then calcined at 400° C. over a period of 3 hours. Then the calcined supports were reduced in a hydrogen stream in a flow apparatus at about 450° C. for a period of 15 hours. The platinum content is 0.3% by weight. The Pt dispersion is 54%, the BET surface area 115 $m^2$/g.

Example 1 (Pt Eggshell Catalyst of the Invention, Prepared Via Incipient Wetness Method)

An aqueous solution of platinum-sulfurous acid (15.1% by weight, based on Pt; from Heraeus) is diluted with water to a concentration of about 0.43% by weight, based on Pt. Subsequently, 70 ml of the diluted solution is contacted at room temperature under continual agitation with 100 g of an alumina support (delta/theta-$Al_2O_3$; spheres with a diameter of 2 to 4 mm, BET 115 $m^2$/g; pore volume 0.8 ml/g; bulk density 560 g/l). The volume of the aqueous solution corresponds at least to the water absorption capacity of the support. After 15 min, the supernatant solution is removed with the aid of an evaporator and the support is dried at 120° C. over a period of eight hours. Then the dried support is calcined at 350° C. over a period of two hours and then reduced in a hydrogen stream at 400° C. for a period of 15 hours. The platinum content is 0.3% by weight; the sulfur content is 0.19% by weight. The Pt dispersion is 29%, the BET surface area 115 $m^2$/g.

Example 2 (Pt Eggshell Catalyst of the Invention, Prepared Via Spray Application)

An aqueous solution of platinum-sulfurous acid (15.1% by weight, based on Pt; from Heraeus) is diluted with water to a concentration of about 0.20% by weight, based on Pt. Subsequently, by the method described in DE102007025356 A1, the diluted solution is applied to an alumina support at 70° C. (gamma-$Al_2O_3$; spheres with a diameter of 1 to 2 mm, BET 290 $m^2$/g; pore volume 0.45 ml/g; bulk density 800 g/l). For this purpose, 150 ml of the 2% platinum-sulfuric acid solution are applied by spraying to 100 g of the support. The support is continually agitated in the fluidized bed during the application. In addition, the support is dried at 120° C. over a period of eight hours. Then the dried support is calcined at 350° C. over a period of two hours and then reduced in a hydrogen stream at 400° C. for a period of 15 hours. The platinum content is 0.3% by weight; the sulfur content is 0.18%. The Pt dispersion is 41%, the BET surface area 290 $m^2$/g.

Example 3

An aqueous solution of platinum-sulfurous acid (15.1% by weight, based on Pt; from Heraeus) is diluted with water to a concentration of about 0.67% by weight, based on Pt. Subsequently, 45 ml of the diluted solution is contacted at room temperature under continual agitation with 100 g of an alumina support (delta/theta-$Al_2O_3$; spheres with a diameter of 2 to 4 mm, BET 35 $m^2$/g; pore volume 0.5 ml/g; bulk density 780 g/l). The volume of the aqueous solution corresponds at least to the water absorption capacity of the support. After 15 min, the supernatant solution is removed with the aid of an evaporator and the support is dried at 120° C. over a period of eight hours. Then the dried support is calcined at 350° C. over a period of two hours and then reduced in a hydrogen stream at 400° C. for a period of 15 hours. The platinum content is 0.3% by weight; the sulfur content is 0.18% by weight. The Pt dispersion is 21%, the BET surface area 35 $m^2$/g.

Example 4

An aqueous solution of platinum-sulfurous acid (15.1% by weight, based on Pt; from Heraeus) is diluted with water to a concentration of about 0.86% by weight, based on Pt. Subsequently, 35 ml of the diluted solution is contacted at room temperature under continual agitation with 100 g of an alumina support (delta/theta-$Al_2O_3$; spheres with a diameter of 2 to 4 mm, BET 5 $m^2$/g; pore volume 0.4 ml/g; bulk density 910 g/l). The volume of the aqueous solution corresponds at least to the water absorption capacity of the support. After 15 min, the supernatant solution is removed with the aid of an evaporator and the support is dried at 120° C. over a period of eight hours. Then the dried support is calcined at 350° C. over a period of two hours and then reduced in a hydrogen stream at 400° C. for a period of 15 hours. The platinum content is 0.3% by weight; the sulfur content is 0.19% by weight. The Pt dispersion is 24%, the BET surface area 5 $m^2$/g.

Example 5 (Measurements of Activity)

The activity of the catalysts is examined as follows. The substrate used is perhydrogenated dibenzyltoluene (H18-DBT). The atmospheric oxygen in a 250 ml three-neck flask with reflux condenser is completely removed by purging with nitrogen. Thereafter, the substrate is brought to a reaction temperature of 310° C. at ambient pressure, and the catalyst is added (ratio of platinum to perhydrogenated dibenzyltoluene of 0.1 mol %). The progress of the reaction is monitored over a period of 2 hours via the amount of hydrogen that forms and the conversion of the liquid starting material (NMR).

Figure 1:
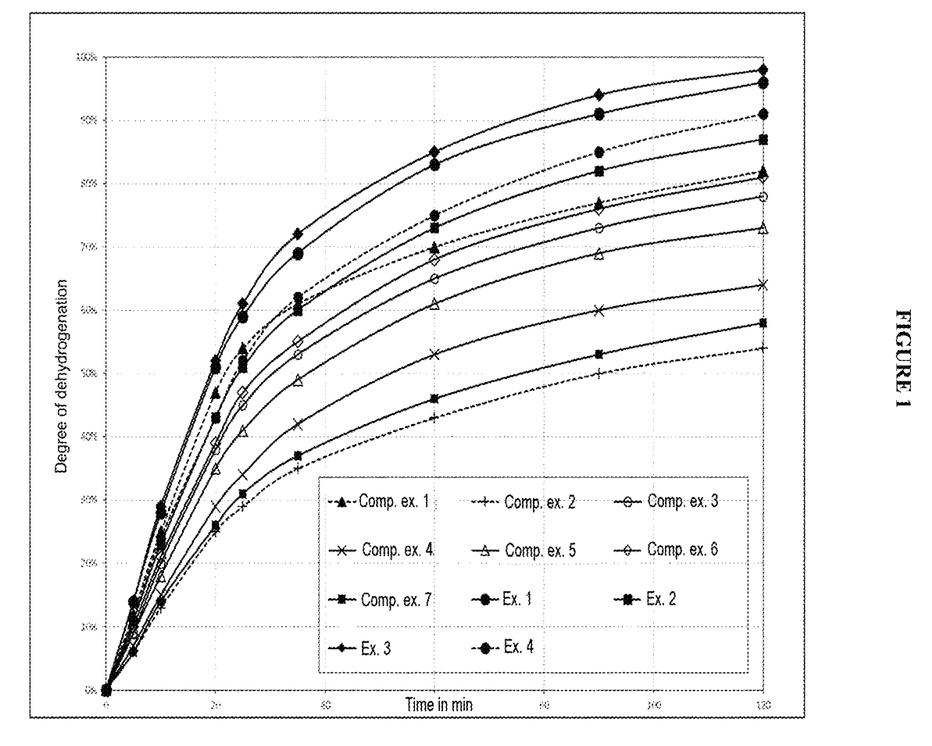

NMR instrument: AVANCE III HD NMR 400 MHz from Bruker;

Solvent:

FIG. 1 shows the degree of dehydrogenation using the catalysts described as a function of time. The improved activity of the catalysts of the invention is clearly apparent by comparison with the comparative catalysts.

The invention claimed is:
1. A shell catalyst comprising
  (a) a shaped support body comprising alumina ($Al_2O_3$),
  (b) platinum in a reduced form in an amount in the range of 0.1-1% by weight, based on the total weight of the shell catalyst, and
  (c) sulfur,
wherein the atomic ratio of platinum to sulfur is 1:1.5-1:10, and wherein the shell catalyst has an outer shell which comprises at least 85 wt. % of the total platinum and at least 85 wt. % of the total sulfur present in the shell catalyst, and wherein the thickness of the outer shell, determined by EDX linescan, is in the range from 40 μm to 250 μm, wherein the shell catalyst has been reduced.

2. The shell catalyst as claimed in claim 1, wherein the shaped support body comprises alumina ($Al_2O_3$) in mixture with one or more of silicon dioxide ($SiO_2$), titanium dioxide ($TiO_2$), zirconium dioxide ($ZrO_2$), and silicon carbide (SiC).

3. The shell catalyst as claimed in claim 1, wherein the shell catalyst has a BET surface area in the range from 1 $m^2$/g to 300 $m^2$/g and a pore volume, determined by Hg intrusion methods to DIN 66133, is 0.1 to 1.0 $cm^3$/g.

4. The shell catalyst as claimed in claim 1, wherein the outer shell comprises at least 95 wt. % of the total platinum and at least 95 wt. % of the total sulfur present in the shell catalyst.

5. The shell catalyst as claimed in claim 1, wherein the shell catalyst has an inner core, and wherein essentially no platinum or sulfur can be detected in the inner core.

6. The shell catalyst as claimed in claim 1, wherein the thickness of the outer shell, determined by EDX linescan, is in the range from 60 μm 125 μm.

7. The shell catalyst as claimed in claim 1, wherein the alumina comprises gamma-alumina, theta-alumina, delta-alumina, alpha-alumina or a mixture of two or more thereof.

8. The shell catalyst as claimed in claim 1, wherein the shell catalyst comprises platinum in an amount in the range of 0.2-1% by weight, based on the total weight of the shell catalyst.

9. The shell catalyst as claimed in claim 1, wherein the atomic ratio of platinum to sulfur is 1:2-1:10.

10. The shell catalyst as claimed in claim 1, wherein
the alumina comprises gamma-alumina, theta-alumina, delta-alumina, alpha-alumina or a mixture of two or more thereof;
the shell catalyst comprises platinum in an amount in the range of 0.2-1% by weight, based on the total weight of the shell catalyst;
the atomic ratio of platinum to sulfur is 1:2-1:10.

11. The shell catalyst as claimed in claim 10, wherein the shaped support body consists essentially of alumina ($Al_2O_3$), the alumina comprising gamma-alumina, theta-alumina, delta-alumina, alpha-alumina or a mixture of two or more thereof.

12. The shell catalyst as claimed in claim 10, wherein the shaped support body consists of alumina ($Al_2O_3$), the alumina comprising gamma-alumina, theta-alumina, delta-alumina, alpha-alumina or a mixture of two or more thereof.

13. The shell catalyst as claimed in claim 10, wherein the shaped support body consists essentially of alumina ($Al_2O_3$) in mixture with one or more of silicon dioxide ($SiO_2$), titanium dioxide ($TiO_2$), zirconium dioxide ($ZrO_2$), and silicon carbide (SiC).

14. The shell catalyst as claimed in claim 10, wherein the shaped support body consists of alumina ($Al_2O_3$) in mixture with one or more of silicon dioxide ($SiO_2$), titanium dioxide ($TiO_2$), zirconium dioxide ($ZrO_2$), and silicon carbide (SiC).

15. A shell catalyst comprising
(a) a shaped support body comprising alumina ($Al_2O_3$),
(b) platinum in a calcined and reduced form in an amount in the range of 0.1-1% by weight, based on the total weight of the shell catalyst, and
(c) sulfur,
wherein the atomic ratio of platinum to sulfur is 1:1.5-1:10, and wherein the shell catalyst has an outer shell which comprises at least 85 wt. % of the total platinum and at least 85 wt. % of the total sulfur present in the shell catalyst, and wherein the thickness of the outer shell, determined by EDX linescan, is in the range from 40 µm to 250 µm, wherein the shell catalyst has been calcined and reduced.

16. A shell catalyst according to claim 15, made by a process comprising:
(a) applying an aqueous solution of platinum sulfite acid ($H_3Pt(SO_3)_2OH$) to a shaped support body to obtain a laden shaped support body,
(b) optionally washing and/or drying the laden shaped support body, wherein the drying is effected at a temperature in the range from 70° C. to 150° C., over a period of 1 h to 15 h,
(c) calcining the optionally washed and/or dried, laden shaped support body at a temperature in the range from 200° C. to 390° C., over a period of 0.25 h to 5 h, to obtain a calcined platinum-containing and sulfur-containing shaped shell catalyst body, and
(d) reducing the calcined platinum-containing and sulfur-containing shaped shell catalyst body in the presence of hydrogen at a temperature in the range from 200° C. to 500° C., over a period of 0.25 h to 5 h.

17. The shell catalyst as claimed in claim 15, wherein
the alumina comprises gamma-alumina, theta-alumina, delta-alumina, alpha-alumina or a mixture of two or more thereof;
the shell catalyst comprises platinum in an amount in the range of 0.2-1% by weight, based on the total weight of the shell catalyst; and
the atomic ratio of platinum to sulfur is 1:2-1:10.

18. The shell catalyst as claimed in claim 17, wherein the shaped support body consists essentially of alumina ($Al_2O_3$).

19. The shell catalyst as claimed in claim 17, wherein the shaped support body consists of alumina ($Al_2O_3$).

20. A process for producing the platinum-containing and sulfur-containing shell catalyst of claim 1, comprising the following steps:
(a) applying a solution, preferably an aqueous solution, of platinum sulfite acid ($H_3Pt(SO_3)_2OH$) to a shaped support body to obtain a laden shaped support body,
(b) optionally washing and/or drying the laden shaped support body, wherein the drying is effected at a temperature in the range from 70° C. to 150° C., over a period of 1 h to 15 h,,
(c) calcining the optionally washed and/or dried, laden shaped support body at a temperature in the range from 200° C. to 390° C., over a period of 0.25 h to 5 h, to obtain a calcined platinum-containing and sulfur-containing shaped shell catalyst body, and
(d) reducing the calcined platinum-containing and sulfur-containing shaped shell catalyst body in the presence of hydrogen at a temperature in the range from 200° C. to 500° C., over a period of 0.25 h to 5 h.

21. A process for partial or complete dehydrogenation of perhydrogenated or partly hydrogenated cyclic hydrocarbons, the process comprising contacting a perhydrogenated or partly hydrogenated cyclic hydrocarbon with the shell catalyst of claim 11 for dehydrogenation, wherein the dehydrogenation is performed at a temperature in the range from 200 to 400° C. and a pressure in the range of 1 to 5 bar.

* * * * *